(12) United States Patent
Kagayama et al.

(10) Patent No.: US 7,816,126 B2
(45) Date of Patent: Oct. 19, 2010

(54) CULTURE OBSERVATION APPARATUS, SAMPLE TRAY HEAT-INSULATING DEVICE AND LID

(75) Inventors: Akitsugu Kagayama, Hachioji (JP); Ryuichi Hirano, Hachioji (JP); Atsuhiro Tsuchiya, Hachioji (JP); Kenichi Koyama, Hachioji (JP); Kazuhiro Hasegawa, Hachioji (JP); Katsuyoshi Yamaguchi, Hachioji (JP); Hideaki Endo, Hachioji (JP)

(73) Assignee: Olympus Corporation, Tokyo (JP)

( * ) Notice: Subject to any disclaimer, the term of this patent is extended or adjusted under 35 U.S.C. 154(b) by 1168 days.

(21) Appl. No.: 11/312,114

(22) Filed: Dec. 20, 2005

(65) Prior Publication Data

US 2006/0141609 A1    Jun. 29, 2006

(30) Foreign Application Priority Data

Dec. 28, 2004    (JP)    ............................. 2004-381523

(51) Int. Cl.
  *C12M 3/00*    (2006.01)
  *C12M 1/34*    (2006.01)

(52) U.S. Cl. ................................. 435/288.7; 435/287.1

(58) Field of Classification Search .............. 435/288.7, 435/287.1
  See application file for complete search history.

(56) References Cited

U.S. PATENT DOCUMENTS

| | | | | |
|---|---|---|---|---|
| 4,339,537 A | * | 7/1982 | Sogi et al. | .................... 435/380 |
| 4,775,628 A | * | 10/1988 | Takakura et al. | ......... 435/305.4 |
| 6,335,824 B1 | * | 1/2002 | Overbeck | .................... 359/368 |
| 6,670,170 B1 | * | 12/2003 | Gaffin et al. | ............. 435/288.4 |
| 2002/0072113 A1 | * | 6/2002 | Barbera-Guillem et al. | ........................ 435/305.1 |
| 2002/0150933 A1 | * | 10/2002 | Ehricht et al. | ................... 435/6 |
| 2004/0241832 A1 | * | 12/2004 | Muraki et al. | ............ 435/287.1 |

FOREIGN PATENT DOCUMENTS

| | | |
|---|---|---|
| JP | 58-155087 B2 | 9/1983 |
| JP | 11-202213 A | 7/1999 |
| JP | 2001-280915 A | 10/2001 |
| JP | 2003-093041 A | 4/2003 |

* cited by examiner

*Primary Examiner*—Walter D Griffin
*Assistant Examiner*—Lydia Edwards
(74) *Attorney, Agent, or Firm*—Holtz, Holtz, Goodman & Chick, PC

(57) ABSTRACT

A culture observation apparatus, which is used for observing a cultured cell while culturing the cell, includes a culture device that forms a culture space which is controlled to be an environment suitable for culturing the cultured cell; a sample tray that holds a container housing the cultured cell and a culture medium; a microscope that serves for observing the cultured cell; a tray holding mechanism that holds the sample tray in the culture space in a detachable manner with good reproducibility; and a shifting mechanism that relatively shifts the sample tray held by the tray holding mechanism and a light axis of the microscope along a plane that is orthogonal to the light axis, wherein the sample tray has a heater used for heating the sample tray, and is electrically connectable to an energy supplying unit that supplies energy to the sample tray.

22 Claims, 11 Drawing Sheets

CULTURE OBSERVATION APPARATUS, SAMPLE TRAY HEAT-INSULATING DEVICE AND LID

CROSS-REFERENCE TO RELATED APPLICATIONS

This application is based upon and claims the benefit of priority from Japanese Patent Application No. 2004-381523, filed on Dec. 28, 2004, the entire contents of which are incorporated herein by reference.

BACKGROUND OF THE INVENTION

1. Field of the Invention

This invention relates to a culture observation apparatus that is used for observing cultured cells while culturing the cells.

2. Description of the Related Art

In the field of biological research, various experiments have been conducted with the use of cultured cells for the study of dynamic changes in living organisms. The cultured cells are placed in a carbon dioxide incubator that is kept at an inner temperature of 37° C., a carbon dioxide gas concentration of 5%, and a humidity of 100%, together with a liquid referred to as a culture medium made from bovine serum or the like, so that the activities of the cultured cells are maintained. Moreover, observation apparatuses, which allow observation while the activities of the cultured cells are maintained with the use of a microscope equipped with functions of the carbon dioxide incubator, have been commercially available.

Cultured cells and a culture medium are generally cultured in a dish that is made of plastic or glass and has a cylindrical form in its outer shape or a petri dish which is available in various shapes.

Some experiments using such cultured cells last a long period of time, in particular, experiments on cell lineage, in which changes in specific cells are traced, is carried out over a long period of time.

The culture medium, however, needs to be changed once approximately every three days. Hence, the long-term observation of a specific cell necessarily accompanies the exchange of culture mediums; which is carried out on a clean bench or the like after the removal of the container containing cultured cells from the microscope.

A shifting section between the microscope and the clean bench and the inside of the clean bench are rarely kept at 37° C. corresponding to the temperature of the culture space inside the carbon dioxide incubator, and normally set to 20 to 25° C. which allow people to work comfortably. Hence, during the culture medium exchanging operation for about 5 minutes, the temperature of the container housing the cultured cells tends to drop to cause damages on the cultured cells inside the container.

SUMMARY OF THE INVENTION

A culture observation apparatus which is used for observing a cultured cell while culturing the cell, according to one aspect of the present invention includes, a culture device that forms a culture space which is controlled to be an environment suitable for culturing the cultured cell; a sample tray that holds a container housing the cultured cell and a culture medium; a microscope that serves for observing the cultured cell; a tray holding mechanism that holds the sample tray in the culture space in a detachable manner with good reproducibility; and a shifting mechanism that relatively shifts the sample tray held by the tray holding mechanism and a light axis of the microscope along a plane that is orthogonal to the light axis, wherein the sample tray has a heater used for heating the sample tray, and is electrically connectable to an energy supplying unit that supplies energy to the sample tray.

A sample tray heat-insulating device that heat-insulates a sample tray which holds a Container housing a cultured cell and a culture medium, according to another aspect of the present invention includes a sample tray mounting base on which the sample tray is mounted; a heater that heats the sample tray mounting base; and a base that rotatably supports the sample tray mounting base.

A lid, which covers a container held on a sample tray and housing a cultured cell and a culture medium, according to still another aspect of the present invention includes a lid main body having an opening; and a transparent plate that seals the opening of the lid main body, wherein the lid main body is mounted on the sample tray, with the lid main body being directly made in contact with the sample tray, so as to cover the container.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Embodiments of the present invention will be described in detail below with reference to the accompanying drawings.

Figure 1:
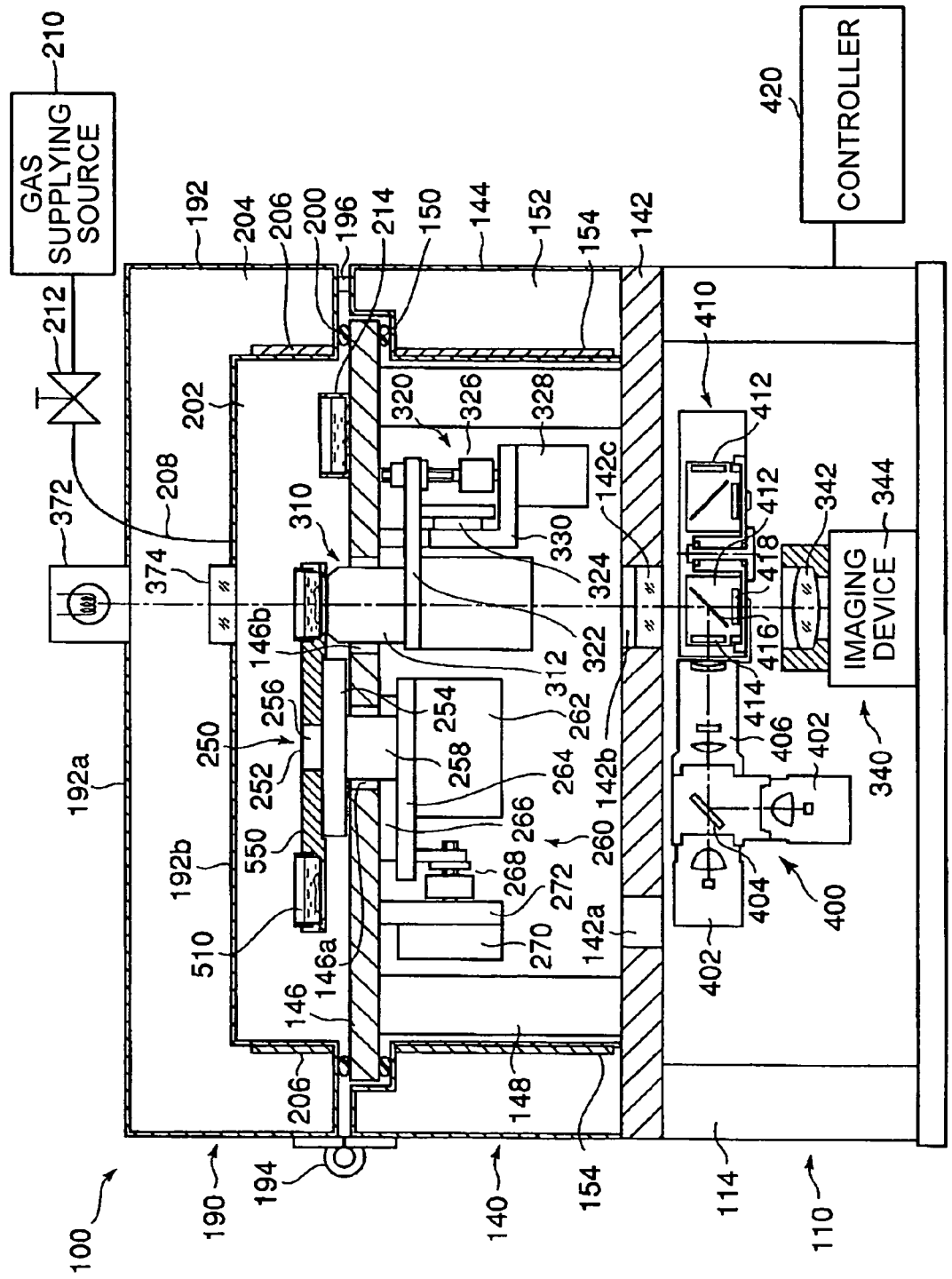
FIG. 1 is a sectional view that schematically shows a culture observation apparatus according to a first embodiment of the present invention.

A first embodiment is directed to a culture observation apparatus for observing a cultured cell while culturing the cultured cell. The culture observation apparatus basically includes a culture device (incubator) used for culturing the cultured cell and a microscope used for observing the cultured cell, which are combined with each other. FIG. 1 is a schematic sectional view of a culture observation apparatus according to the first embodiment of the present invention.

As shown in FIG. 1, the culture observation apparatus 100 includes a culture device main body 190, a culture device sub-main body 140, and a main-body supporting base 110 that supports these.

The main-body supporting base 110 has a plurality of leg members 114.

The culture device sub-main body 140 is provided with a lower base portion 142 that is supported by the leg members 114, a side wall 144 that surrounds the upper periphery of the lower base portion 142, and an upper base portion 146 that covers an opening on the upper side of the side wall 144.

The upper base portion 146 is supported by a plurality of supporting pillars 148 that stand on the lower base portion 142. The upper base portion 146 and the side wall 144 are made in contact with each other through a seal member 150, with a gap between these being kept in an air-tight state. The side wall 144 has a hollow structure including a heat-insulating space 152, and a heater 154 is installed inside the heat-insulating space 152 of the side wall 144. The lower base portion 142 has a through hole 142a having a diameter of about 30 mm, which allows the inner space of the culture device sub-main body 140 to communicate with outside air.

The culture device main body 190 is provided with a box-shaped case member 192 with an opening on the bottom face. The case member 192 is attached to the side wall 144 by hinges 194 so as to be opened and closed with respect to the culture device sub-main body 140. A seal member 200 is placed between the case member 192 and the upper base portion 146, and when closed, the case member 192 is made in contact with the upper base portion 146 through the seal member 200, with a gap between the case member 192 and the upper base portion 146 being kept in an air-tight state. The case member 192 has a hollow structure including a heat-insulating space 204, and a heater 206 is installed inside the heat-insulating space 204 of the case member 192.

When the case member 192 is closed, the culture device sub-main body 140 and the culture device main body 190 are allowed to form a culture space 202 used for culturing a sample. The culture observation apparatus 100 is provided with an open/close sensor 196 for sensing the opening and closing of the case member 192.

A gas supplying flow path 208, used for supplying a gas such as a carbon dioxide gas to the culture space 202, is connected to the case member 192. The gas supplying flow path 208 is connected to a gas supplying source 210, and a valve 212 used for controlling the amount of supply of the gas is installed in the middle of the gas supplying flow path 208.

The culture observation apparatus. 100 is provided with a tray attaching unit 252 to which a sample tray 550 is attached and a horizontal shifting mechanism 260 used for shifting the tray attaching unit 252 horizontally inside the culture space 202.

The tray attaching unit 252 has a tray receiving unit 254 that receives the sample tray 550, a protruding portion 256 that protrudes upward from the tray receiving unit 254 and a rotation shaft 258 that extends downward from the tray receiving unit 254. The rotation shaft 258 is rotatably supported by a mechanism not shown.

The upper base portion 146 has a through hole 146a, and the rotation shaft 258 of the tray attaching unit 252 extends through the through hole 146a of the upper base portion 146. A gap between the upper face of the upper base portion 146 and the lower face of the tray receiving unit 254 is preferably set to 0.1 mm or less in order to preferably suppress a leak of moisture. Moreover, in order to further suppress the leak of moisture, an elastic member may be placed between the upper face of the upper base portion 146 and the lower face of the tray receiving unit 254.

The horizontal shifting mechanism 260 is provided with a motor 262 used for rotating the tray attaching unit 252, a motor supporting member 264 that supports the motor 262, a linear guide 266 that shiftably supports the motor supporting member 264, a ball screw 268 that is engaged with the motor supporting member 264, a motor 270 used for driving the ball screw 268, and a motor supporting member 272 that supports the motor 270.

The motor supporting member 264 is attached to the upper base portion 146 through the linear guide 266, and allowed to shift laterally with respect to the upper base portion 146. Here, the motor supporting member 272 is secured to the upper base portion 146. Moreover, the ball screw 268 converts a rotation movement of the shaft of the motor 270 to a linear movement of the motor supporting member 264.

The microscope is provided with an objective optical unit 310 and an image-forming optical unit 340. The objective optical unit 310 is housed inside the culture device sub-main body 140. The image-forming optical unit 340 is placed on a lower outer portion of the culture device sub-main body 140.

The objective optical unit 310 is provided with an objective lens 312 and a focusing mechanism 320 used for shifting the objective lens 312 upward and downward.

The focusing mechanism 320 is provided with an objective lens supporting member 322 that supports the objective lens 312, a linear guide 324 that shiftably supports the objective lens supporting member 322, a ball screw 326 that is engaged with the objective lens supporting member 322, a motor 328 used for driving the ball screw 326, and a motor supporting member 330 that supports the motor 328.

The motor supporting member 330 is secured to the upper base portion 146. The objective lens supporting member 322, which is attached to the motor supporting member 330 through the linear guide 324, is capable of shifting upward and downward with respect to the motor supporting member 330. The ball screw 326 converts a rotation movement of the shaft of the motor 328 to a linear movement of the objective lens supporting member 322.

The upper base portion 146 has a through hole 146b, and the objective lens 312 extends through the through hole 146b of the upper base portion 146. A gap between the through hole 146b of the upper base portion 146 and the objective lens 312 is preferably set to 0.1 mm or less in order to preferably suppress a leak of moisture. Moreover, in order to further suppress the leak of moisture, an elastic member may be placed between the through hole 146b of the upper base portion 146 and the objective lens 312.

The image-forming optical unit 340 is provided with an image-forming lens 342 and an imaging device 344. The lower base portion 142 has a through hole 142b, and an optical window 142c is formed in the through hole 142b in a tightly-sealed state. The image-forming optical unit 340 is optically coupled to the objective lens 312 through the optical window 142c formed in the lower base portion 142.

Moreover, the microscope is provided with a transmissive lighting optical system used for providing transmissive lighting of the sample 510. The transmissive lighting optical system is provided with an illuminating light source 372 that is attached to an outer wall 192a of the case member 192 in a tightly-sealed state, and an optical window 374 that is formed in an inner wall 192b of the case member 192 in a tightly-sealed state. Both of the illuminating light source 372 and the optical window 374 are located above the objective lens 312. The illuminating light source 372 emits illuminating light, and the optical window 374 allows the illuminating light to pass therethrough.

Moreover, the microscope is provided with an excitation lighting optical system used for exciting the sample. The excitation lighting optical system has an exciting light source 400 and a fluorescent cube unit 410.

The exciting light source 400 includes a plurality of exciting light sources 402, and these emit light rays having different wavelengths. The exciting light source 400 further includes an element 404 that unifies light paths extending from the exciting light sources 402 into one path and a projection tube 406 that directs light rays from the element 404 to the fluorescent cube unit 410.

The fluorescent cube unit 410 includes a plurality of fluorescent cubes 412. The fluorescent cubes 412 are held, for example, in a rotatable turret, and one of the fluorescent cubes 412 is selectively positioned on a light path between the objective optical unit 310 and the image-forming optical unit 340. Each of the fluorescent cubes 412 is provided with a fluorescent filter 414, a dichroic mirror 416, and an absorbing filter 418. The fluorescent filter 414 selectively transmits light rays having specific wavelengths to generate an excited light ray. The dichroic mirror 416 reflects the excited light ray that has been transmitted through the fluorescent filter 414, and also selectively transmits fluorescent light generated from the sample 510. The absorbing filter 418 selectively transmits light rays having specific wavelength ranges in the fluorescent light that has been transmitted through the dichroic mirror 416 so that undesired wavelength components are removed therefrom.

The culture observation apparatus 100 is further provided with a control unit 420 that controls the entire apparatus. The control unit 420 controls, for example, the horizontal shifting mechanism 260, the focusing mechanism 320, the heater 154, the heater 206, the fluorescent cube units 410, the exciting light sources 402 and the illuminating light source 372.

Figure 2:
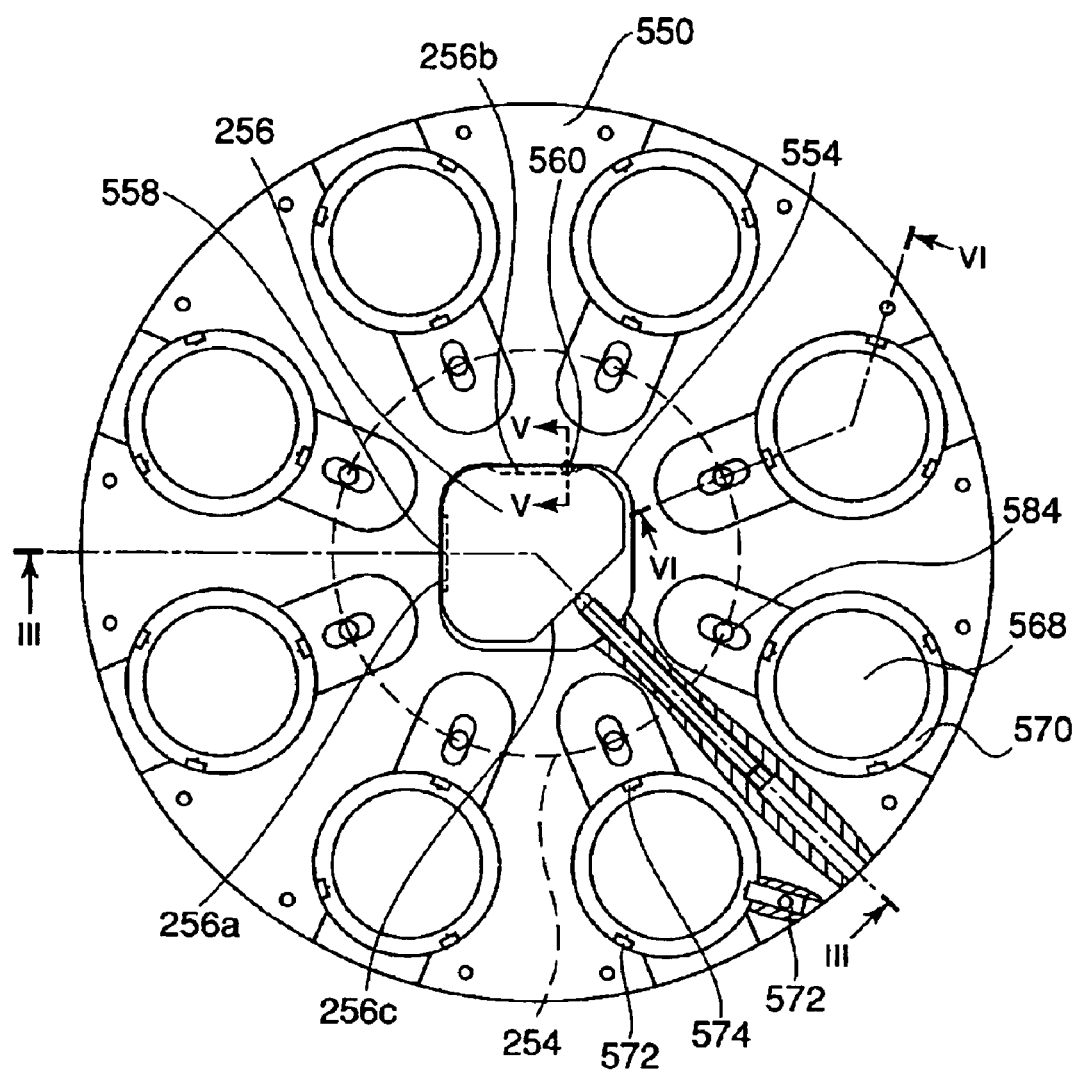
FIG. 2 is a plan view of a sample tray shown in FIG. 1.
Figure 3:
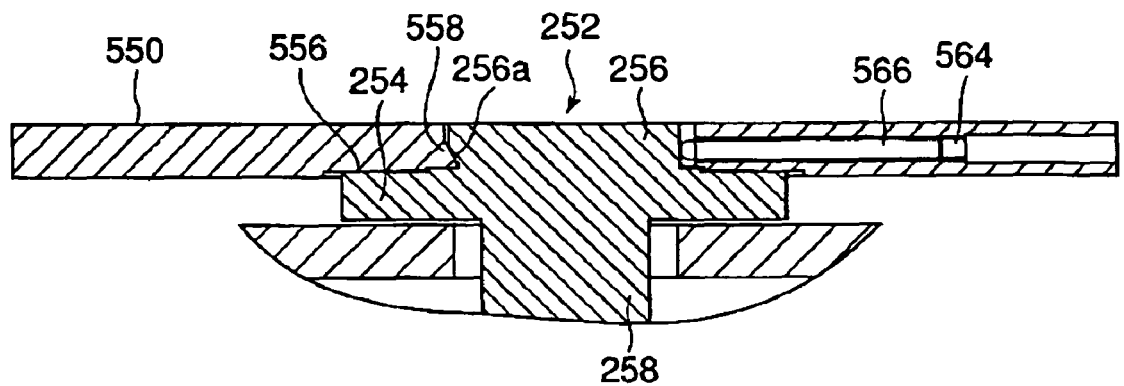
FIG. 3 is a sectional view taken along line III-III of FIG. 2.
Figure 4:
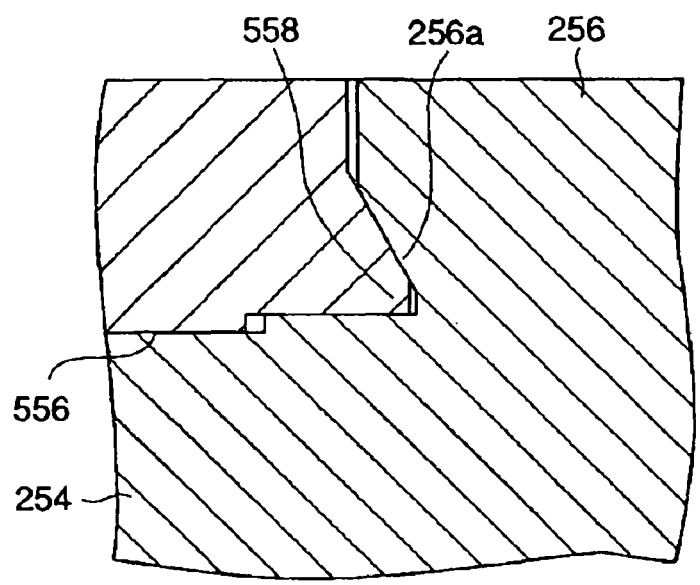
FIG. 4 is an enlarged view of a portion of FIG. 3.
Figure 5:
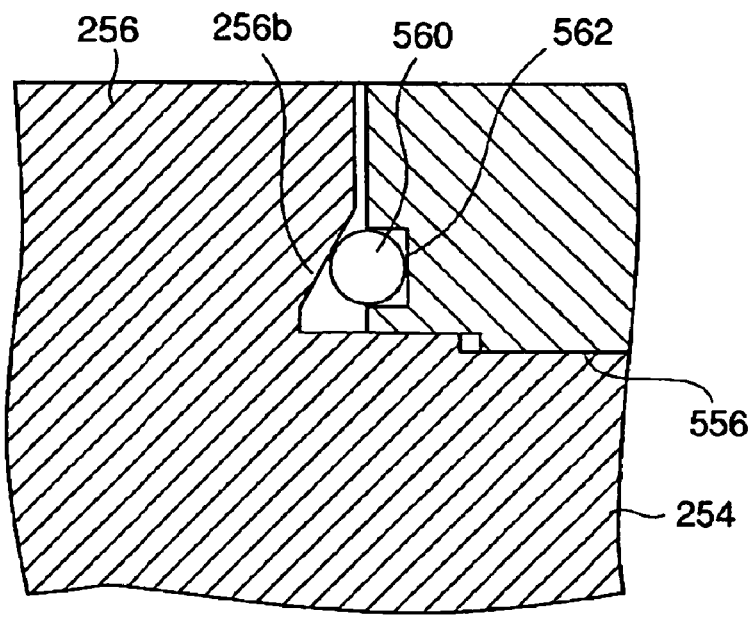
FIG. 5 is a sectional view taken along line V-V of FIG. 2.

FIG. 2 is a plan view of the sample tray shown in FIG. 1. FIG. 3 is a sectional view taken along line III-III of FIG. 2. FIG. 4 is an enlarged view of one portion of FIG. 3. FIG. 5 is a sectional view taken along line V-V of FIG. 2.

As shown in FIG. 2, the tray receiving unit 254 of the tray attaching unit 252 has a round shape, and the upper face thereof is orthogonal to the light axis of the objective lens 312. The protruding portion 256 of the tray attaching unit 252 has a substantially pentagonal shape. The protruding portion 256 has two male dovetails 256a and 256b that are respectively formed on the two side faces orthogonal with each other. Each of the male dovetails 256a and 256b has a slope that tilts outward at approximately 60 degrees. Moreover, the protruding portion 256 is provided with a pressing face 256c that is orthogonal to the two side faces respectively having the male dovetails 256a and 256b. The pressing face 256c is substantially orthogonal to the bisector of each of the two side faces having the respective male dovetails 256a and 256b.

The sample tray 550 is provided with an opening 554 that has a substantially rectangular shape and is formed in the center, and a depressed plane 556 that has a round shape and is formed on the bottom face outside of the opening 554. The opening 554 is larger than the protruding portion 256 so that the protruding portion 256 is allowed to pass through the opening 554. The depressed plane 556 is larger than the tray receiving unit 254 so that the upper face of the tray receiving unit 254 can be made in face-contact with the depressed plane 556.

As shown in FIGS. 3 and 4, the sample tray 550 is provided with a female dovetail 558 that is made in face-contact with the male dovetail 256a of the protruding portion 256, and formed on the side face of the opening 554 that faces the male dovetail 256a of the protruding portion 256.

As shown in FIG. 5, the sample tray 550 also has a depressed portion 562 that receives a ball 560 that is placed in contact with the male dovetail 256b, and formed on the side face of the opening 554 that faces the male dovetail 256b of the protruding portion 256.

As shown in FIGS. 2 and 3, the sample tray 550 is provided with a female screw 564 that extends between the outer peripheral side face and the side face of the center opening 554, and a fixed screw 566 that is meshed with the female screw 564. The female screw 564 and the fixed screw 566 form pressing unit that press the pressing face 256c of the protruding portion 256. Moreover, together with the opening 554, the pressing unit forms a gripping mechanism that grips the protruding portion 256 of the tray attaching unit 252, and the gripping mechanism forms a tray holding mechanism 250 in cooperation with the tray attaching unit 252.

The sample tray 550 is attached to the tray attaching unit 252 in the following manner.

The sample tray 550 is mounted on the tray attaching unit 252 with the fixed screw 566 drawn therein. In this state, the bottom face of the sample tray 550 is made in face-contact with the tray receiving unit 254, with the protruding portion 256 being positioned inside the opening 554 of the sample tray 550. The fixed screw 566 is bolted to be pressed against the pressing face 256c. The sample tray 550 is shifted by the resulting reaction force, and pushed against the protruding portion 256.

The fixed screw 566 is bolted appropriately so that the sample tray 550 is secured onto the tray attaching unit 252. In this state, by an interaction between the male dovetail 256a and the female dovetail 558 as well as by an interaction among the male dovetail 256b, the ball 560, and the depressed portion 562, the depressed plane 556 of the sample tray 550 is positively pushed against the upper face of the tray receiving unit 254 so that the sample tray 550 is maintained horizontally. In other words, the sample tray 550 is placed in such a manner that the upper face thereof is made in parallel with the plane that is orthogonal to the light axis of the objective lens 312. Moreover, since the sample tray 550 is made in contact with the tray attaching unit 252 through one face of the female dovetail 558 and the ball 560, the sample tray 550 is always secured onto the tray attaching unit 252 with good reproducibility.

Figure 6:
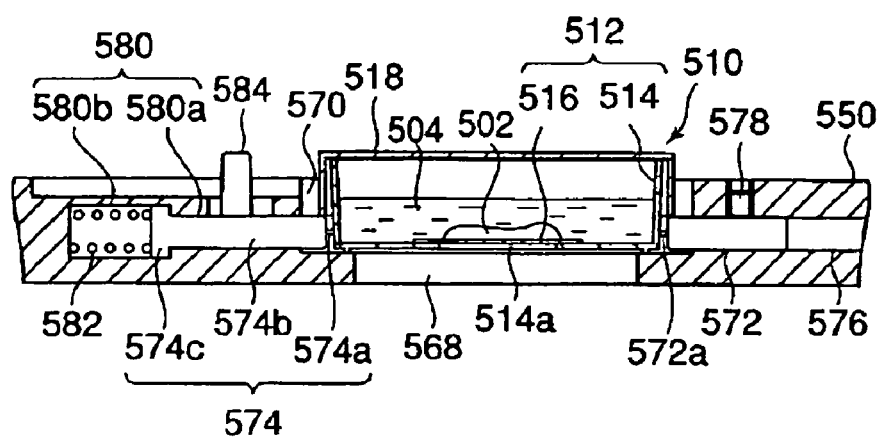
FIG. 6 is a sectional view taken along line VI-VI of FIG. 2.

FIG. 6 is a sectional view taken along line VI-VI of FIG. 2. FIG. 6 includes the sample drawn together with the apparatus.

As shown in FIG. 6, the sample 510 includes a container 512 housing a cultured cell 502 and a culture medium 504, and a lid 518 covering the container 512. The container 512 and the lid 518 are both optically transparent.

The container 512 includes a container main body 514 and a cover glass 516. The container main body 514 is a Schale-shaped plastic container having a diameter of 35 mm, with an opening 514a having a diameter of about 10 mm formed in the bottom portion. The cover glass 516 is a cover glass having a thickness of 0.17 mm, which has been widely used in the microscope field, and closes the opening 514a of the bottom portion of the container main body 514.

The objective lens 312 requires a high NA for brightness and resolution. In general, an objective lens with a high NA is optimally designed to be used with a cover glass having a thickness of 0.17 mm. Since the container 512 has a cover glass of 0.17 mm in thickness at a portion facing the objective lens 312, a generally-used objective lens with a high NA can be used as the objective lens 312.

The sample tray 550 has a plurality of openings 568 that allow observation through the objective lens 312 from below and depressed portions 570 formed around respective openings 568. The openings 568 are positioned along the circumference with a diameter of approximately 160 mm. The opening 568, which has a diameter of approximately 25 mm, has such a size that, with respect to relative shifts of the sample tray 550 and the objective lens 312, the two members are prevented from intervening with each other. The diameter of the depressed portion 570 is approximately 40 mm, which is slightly larger than the diameter of the container 512. The container 512 is placed inside the depressed portion 570 so that the depressed portion 570 supports the container 512.

Moreover, the sample tray 550 is provided with a container holding mechanism used for holding the container 512 on each of the depressed portions 570. The container holding mechanism is provided with two fixed container holding members 572, a shiftable container holding member 574, and a coil spring 582 that is pressing the container holding member 574.

Two container holding members 572 and the single container holding member 574 are placed around the depressed portion 570. The container holding members 572 and the container holding member 574 are arranged at equal intervals, that is, with an angular interval of 120 degrees. The container holding member 572 has a contact portion 572a that is made in contact with the container 512, and the contact portion 572a has a sharp tip. The tip of the contact portion 572a has, for example, a diameter of about 50 µm. Moreover, the container holding member 574 has a contact portion 574a that is made in contact with the container 512, and the contact portion 574a has a sharp tip. The tip of the contact portion 574a has, for example, a diameter of about 50 µm.

The container holding member 572, which has a column shape, is housed into a hole 576 that is formed in the sample tray 550, and secured by a fixed screw 578. The securing position of the container holding member 572 is changeable, and adjusted in accordance with the size of the container 512.

The container holding member 574 is provided with a column-shaped main-body portion 574b, and an end portion 574c having a column shape that has a size larger than the main-body portion 574b. The container holding member 574 is housed in a hole 580 formed in the sample tray 550, and allowed to freely shift inside the hole 580. The hole 580 has a small-diameter portion 580a and a large-diameter portion 580b so that the main-body portion 574b of the container holding member 574 is housed in the small-diameter portion 580a and the end portion 574c of the container holding member 574 is housed in the large-diameter portion 580b. A coil spring 582 is arranged inside the large-diameter portion 580b, and the coil spring 582 presses the end portion 574c. A knob 584 is secured to the main-body portion 574b of the container holding member 574, and the knob 584 protrudes from the upper face of the sample tray 550. With the manipulation of the knob 584, the container holding member 574 can be shifted against the elastic force of the coil spring 582.

Upon securing the container 512, the container holding member 574 is retreated by the manipulation of the knob 584, and after the container 512 is placed on the bottom of the depressed portion 570, the knob 584 is released. Thus, the container 512 is pressed by the container holding member 574, and made in contact with the two container holding members 572. Since the container holding member 574 continues to press the container 512 by a predetermined force that is determined by the coil spring 582, the container 512 is held by the two container holding members 572 and the single container holding member 574.

Since both of the contact portion 572a of the container holding member 572 and the contact portion 574a of the container holding member 574 have a tip having a diameter of about 50 µm, these contact portions cut into the container 512. For this reason, though the container 512 has a shape expanding upward from the bottom face, it is positively held without being push and displaced upward. With this arrangement, upon removing the lid 518 from the container 512 for the exchange of culture mediums or the like, the container 512 is prevented from unexpectedly moving and rotating. In other words, the operations such as exchanging culture mediums can be carried out without the necessity of shifting the position of the container 512. Moreover, since the portion close to the bottom face of the container 512 is pressed, the lid of the attached container may also be utilized.

Upon using the culture observation apparatus 100, the sample tray 550 holding a plurality of samples 510 is attached to the tray attaching unit 252, and a humidifying pad 214 containing pure water is placed in the culture space 202. The culture space 202 is controlled to 37° C. in its inside temperature by the heater 206, and also to 5% in its carbon dioxide concentration by the valve 212. The inner space of the culture device sub-main body 140 is controlled to 37° C. in its inside temperature by the heater 154.

Since the culture space 202 is hardly influenced by the outside air by the heat-insulating space 204 of the case member 192, and since the inner space of the culture device sub-main body 140 is kept at 37° C., the inner temperature of the culture space 202 is favorably maintained at 37° C. Moreover, since the moisture generated in the culture space 202 is hardly leaked outside, the inside of the culture space 202 is maintained at a high moisture state close to 100%.

Since the through hole 142a that connects the inner space of the culture device sub-main body 140 to the outside space has a small diameter, only a little outside air is allowed to flow into the culture device sub-main body 140. Moreover, since the inner space of the culture device sub-main body 140 is enclosed by the heat-insulating space 152, it is hardly influenced by the outside air. For this reason, the objective lens 312 and the focusing mechanism 320, placed inside the culture device sub-main body 140, are desirably maintained at 37° C. without being influenced by the outside air. When the objective lens 312 and the focusing mechanism 320 are influenced by temperatures, defocusing tends to occur easily; however, since this structure maintains the temperature of the objective lens 312 and the focusing mechanism 320 at a constant temperature, it is possible to favorably prevent the occurrence of defocusing.

Even if slight moisture invades inside the culture device sub-main body 140 from the culture space 202, since the moisture is diffused into the outside air through the through hole 142*a*, the inside of the culture device sub-main body 140 is maintained at a low level of moisture. Consequently, it becomes possible to prevent the objective lens 312 from dew condensation and also to prevent the focusing mechanism 320 from rusting.

Upon observation, the sample 510 located above the objective lens 312 is observed. The sample 510 to be observed can be switched with the substantial rotation of the sample tray 550 by the horizontal shifting mechanism 260. The observation site within the sample 510 is adjusted by the shift of the sample tray 550 along the plane orthogonal to the light axis of the objective lens 312 by the horizontal shifting mechanism 260. This adjustment is achieved through the combination of the rotation and the translational shift of the sample tray 550. The rotation and the translational shift are carried out within a range in which the tip of the objective lens 312, located inside the opening 568, is kept from contacting the sample tray 550.

In the first embodiment, the diameter of the container 512 is 35 mm, and eight samples 510 are arranged on the sample tray 550 along the circumference having a diameter of 160 mm. Since the switching process of the samples 510 is carried out by the rotation of the sample tray 550, no translational shift of the sample tray 550 is required to switch the samples 510. Although the sample tray 550 is translation-shifted so as to adjust the observation position, the amount thereof is limited to approximately 10 mm. Therefore, there is only a little space that allows the sample tray 550 to shift.

The following description will discuss a comparative example in which nine samples 510 are arranged in a lattice format with longitudinal and lateral positions of 3×3, and switched by using X and Y stages. In this case, translational shifts of the X and Y stages of 80 mm or more are required for the respective X and Y directions. In contrast, in the first embodiment, the sample tray 550 requires no translational shift for switching the samples 510, and only the translational shift of approximately 10 mm is required for the adjustment of the observation position. Therefore, in comparison with the device using the X and Y stages, the space required for the switching of the samples 510 and the adjustment of the observation position is reduced greatly. This is advantageous in achieving a small-size apparatus at low costs.

Moreover, upon carrying out a long-term observation, an exchange of culture mediums is required. The exchange of culture mediums is carried out with each of the sample trays 550 being removed from the tray attaching unit 252. In other words, during the exchange of culture mediums, the container 512 and the edge portion 519 of the lid 518 are maintained on the sample tray 550, and firmly secured by the container holding mechanism so that no positional deviations occur. After the exchange of culture mediums, the sample tray 550 is attached again to the tray attaching unit 252 in the same state as the state before the exchange of culture-mediums.

In this manner, the first embodiment makes it possible to exchange culture mediums without the necessity of removing the container 512 from the sample tray 550 and also to attach the sample tray 550 to the tray attaching unit 252 with good positional reproducibility; therefore, the container 512 is properly placed at the original position. Thus, it becomes possible to observe a specific cell for a long time.

In the culture observation apparatus 100, the culture medium exchanging operation is carried out through a sequence of processes in which: the sample tray 550 holding a plurality of samples 510 is detached from the tray attaching unit 252 and shifted to a clean bench on which the culture mediums are exchanged, and transferred onto the culture observation apparatus 100 to be attached to the tray attaching unit 252. Here, the culture mediums are exchanged through a sequence of processes in which: the lid 518 of the sample 510 is opened, the old culture medium is drawn out, a new culture medium is placed inside, and the lid 518 of the sample 510 is closed. This operation is repeated as many times as the number of the samples 510.

The cultured cells die unless they are kept at approximately 37° C. which is close to the inner body temperature. If the temperature falls below 36.5° C. even for a short time, the cultured cells will be surely damaged. Here, since the sample 510 and the sample tray 550 are physically made in contact with each other, the temperatures of both of the members are virtually coincident.

The shifting section between the culture observation apparatus 100 and the clean bench and the inside of the clean bench are rarely kept at 37° C. corresponding to the temperature of the culture space, and normally set to 20 to 25° C. which allow people to work comfortably. Hence, during the culture medium exchanging operation for about 5 minutes, the temperatures of the sample tray 550 and the sample 510 tend to drop to damage the cultured cells inside the sample 510.

Figure 7:
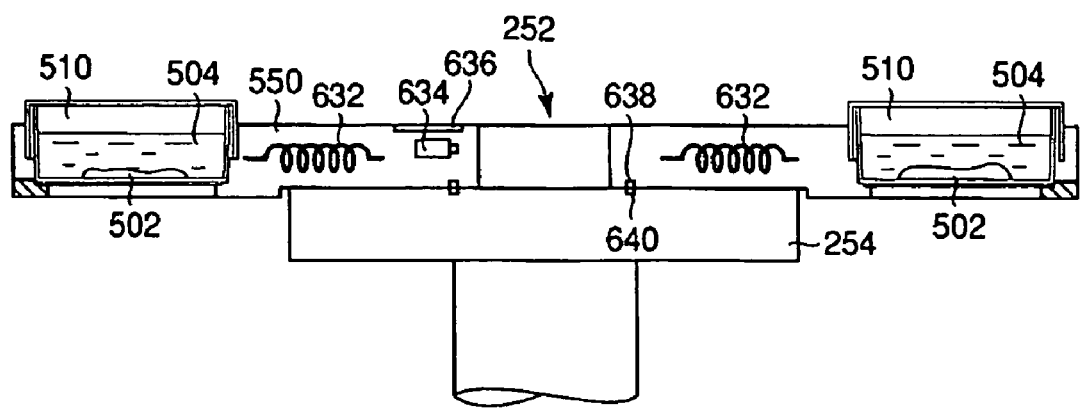
FIG. 7 is a sectional view that schematically shows an inner structure of the sample tray shown in FIG. 1.
Figure 8:
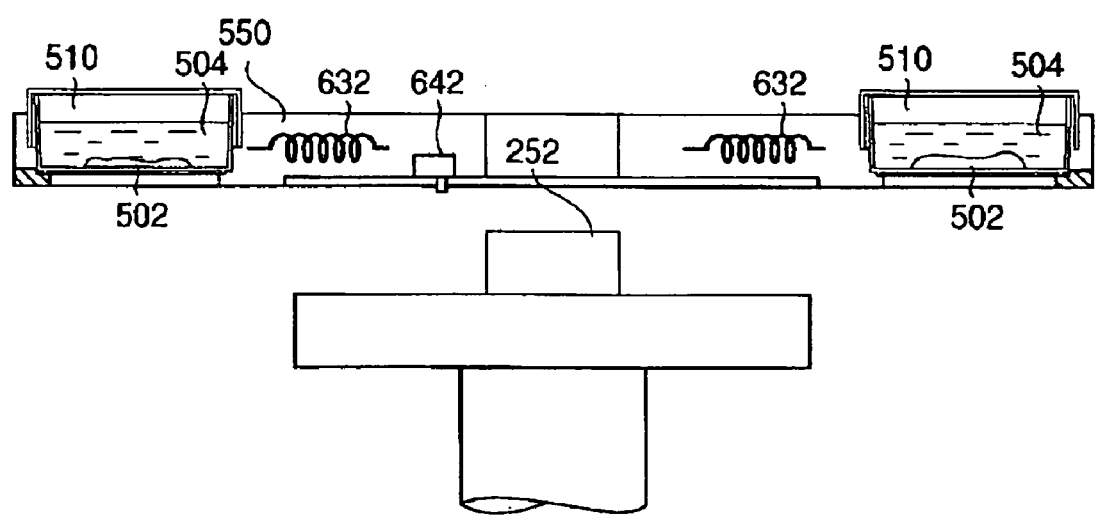
FIG. 8 is another sectional view that schematically shows the inner structure of the sample tray shown in FIG. 7.

Referring to FIGS. 7 and 8, the following description will discuss countermeasures to prevent the cultured cells 502 in the sample 510 from being damaged in the culture medium exchanging operation. FIG. 7 schematically shows the inner structure of the sample tray shown in FIG. 1. FIG. 8 schematically shows the inner structure of the sample tray of FIG. 7 in a different section.

As shown in FIG. 7, the sample tray 550 is provided with a heater 632 that heats the sample tray 550 and an energy storing unit 634 used for driving the heater 632. The heater 632 is placed inside the sample tray 550, and the energy storing unit 634, which is housed inside the sample tray 550, is closed in a liquid-tight state by a waterproof lid 636. Although not particularly limited, the energy storing unit 634 is prepared, for example, as a recharging-type battery that stores electric power. The heater 632 may be prepared, for example, as a resistor that generates heat in response to a power supply; however, not limited to this, any desired electric element that is temperature-adjustable, such as a Peltier element, may be used.

The tray attaching unit 252 of the tray holding mechanism 250 has an energy supplying unit 640 used for supplying energy (for example, electric power) stored in the energy storing unit 634 in the sample tray 550. The energy supplying unit 640 is placed on the upper face of the tray receiving unit 254, and electrically connected to a power supply, not shown. The sample tray 550 is provided with a connector 638 which, when attached to the tray attaching unit 252, is electrically connected to the energy supplying unit 640 of the tray attaching unit 252. With this arrangement, energy (for example, electric power) is accumulated in the energy storing unit 634, while the sample tray 550 is attached to the tray attaching unit 252, that is, during the cultivation and observation of the cultured cells 502 in the sample 510.

As shown in FIG. 8, the sample tray 550 is also provided with a switch 642 used for controlling a supply of energy from the energy storing unit 634 to the heater 632. The switch 642, which is, for example, a pressure sensitive switch, starts supplying energy from the energy storing unit 634 to the heater 632, when the sample tray 550 is separated from the tray receiving unit 254 of the tray attaching unit 252, and stops supplying the energy from the energy storing unit 634 to the heater 632, when the sample tray 550 is received by the tray receiving unit 254 of the tray attaching unit 252.

With this arrangement, during a sequence of operations for exchanging culture mediums, that is, during a shift from the culture observation apparatus 100 to the clean bench and operations in the clean bench, the heater 632 receives an energy supply from the energy storing unit 634, and generates heat so that the temperature in the sample tray 550 is kept at about 37° C. Thus, it is possible to effectively prevent cultured cells 502 in the sample 510 held in the sample tray 550 from being exposed to an inappropriate temperature and consequently damaged.

Figure 9:
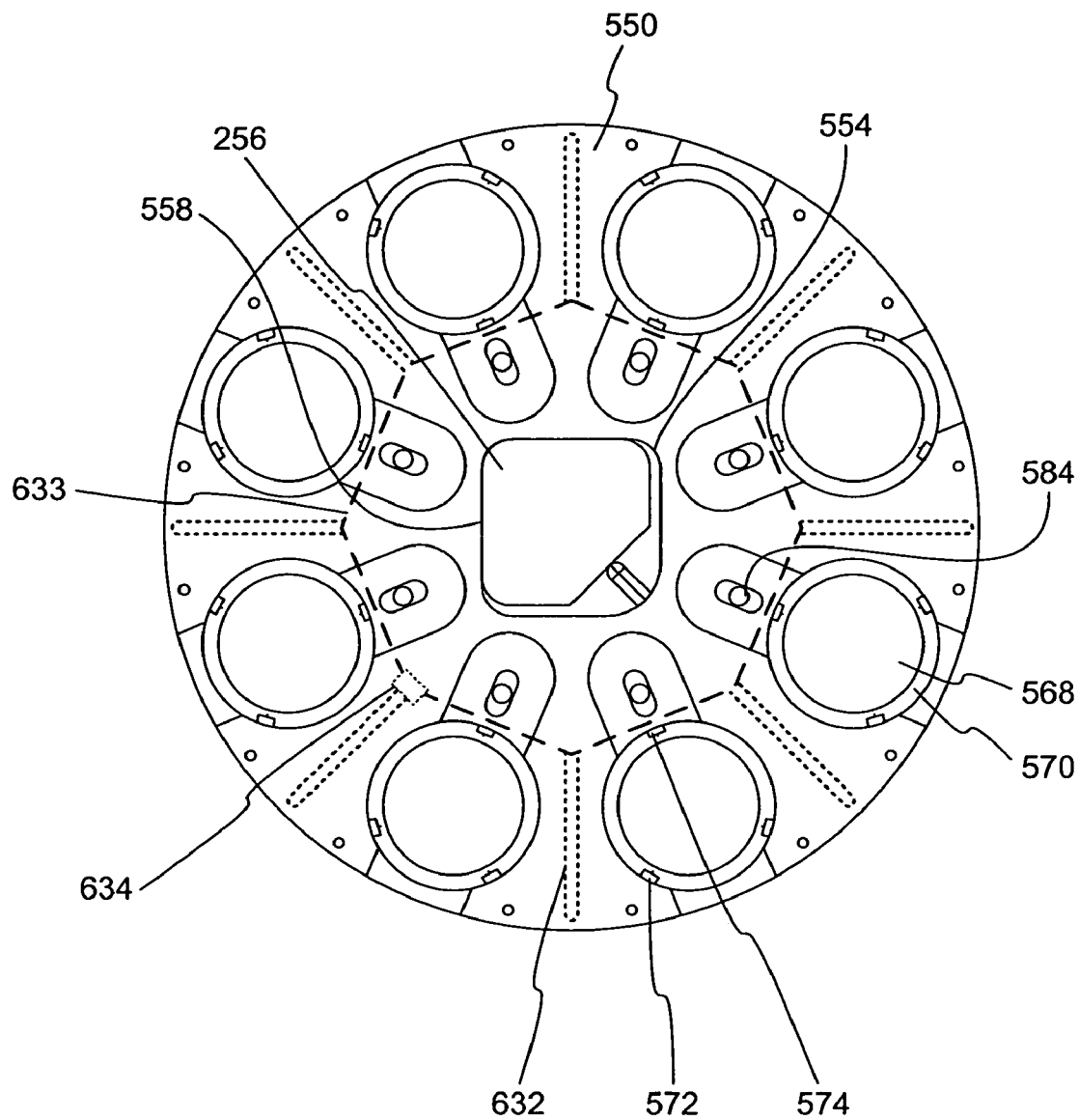
FIG. 9 is a plan view of an example of a sample tray on which a heater is placed.
Figure 10:
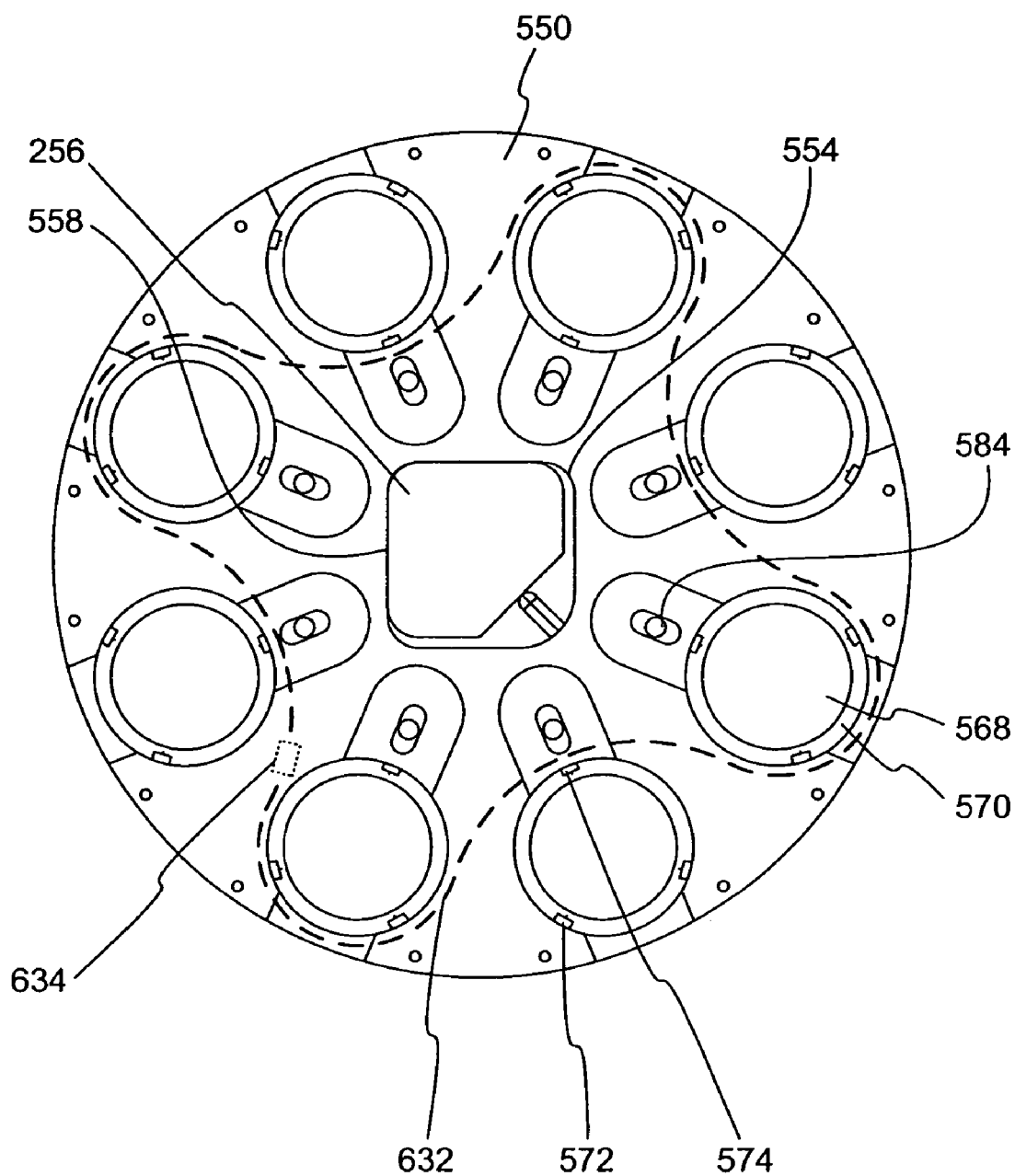
FIG. 10 is a plan view of another example of the sample tray in which the layout of the heater is changed.
Figure 11:
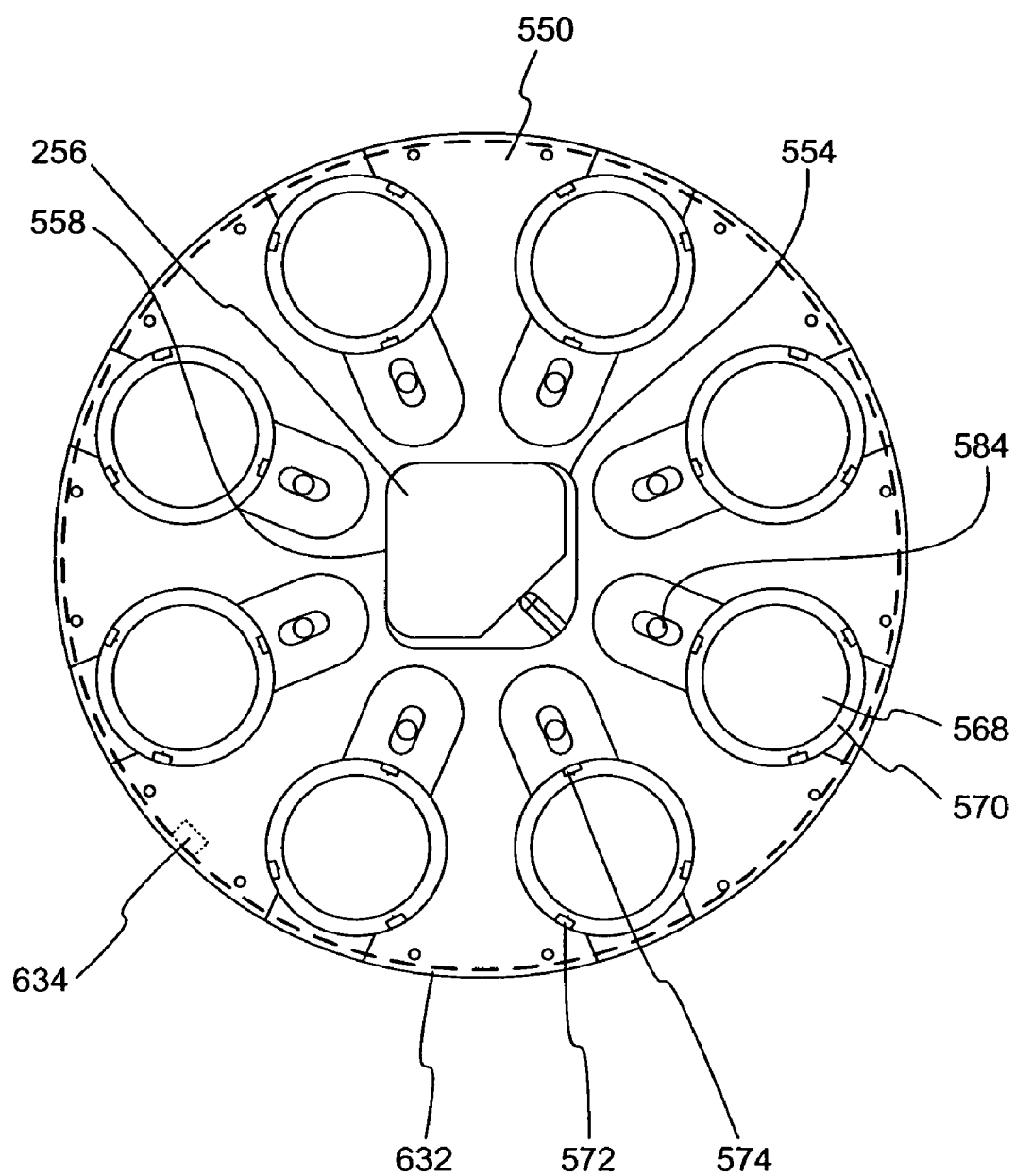
FIG. 11 is a plan view of still another example of the sample tray in which the layout of the heater is changed.

Referring to FIGS. 9, 10 and 11, the following description will discuss a specific example of a system in which the heater 632 is placed on the sample tray 550. FIG. 9 is a plan view of the sample tray 550 in which the heater 632 is placed. FIGS. 10 and 11 are plan views of the sample tray 550 in which the layout of the heater 632 is changed.

In the sample tray 550 shown in FIG. 9, heaters 632 are formed in an annular form and located closer to the center of the sample tray 550 than a plurality of openings 568 positioned on the circumference, and heaters 632 further extend radially from the annular portion between the openings 568. In the sample tray 550 shown in FIG. 10, the heaters 632, which are located closer to the center of the sample tray 550 than the openings 568 positioned on the circumference, and the heaters 632, which are located closer to the outer periphery of the sample tray 550 than the openings 568, are arranged alternately so that they together form an annular shape with outward-protruding portions and inward-receding portions as a whole. Moreover, in the sample tray 550 shown in FIG. 11, the heaters 632 are formed into a circumferential shape and located closer to the outer periphery of the sample tray 550 than the openings 568 positioned on the circumference thereof. The heaters 632, shown in FIGS. 9 to 11, are electrically connected to the energy storing unit 634 that supplies energy to the heaters 632.

In order to arrange the heaters 632 inside the sample tray 550, the sample tray 550 is formed by two discs with sheet-shaped heaters 632 being sandwiched inbetween, for example. Moreover, in order to effectively transmit heat generated in the heaters 632, the sample tray 550 may be formed from metal such as aluminum, with an insulating film or the like being formed on the periphery of each of the heaters 632, so as to prevent the heaters 632 from conducting to the other portions of the sample tray 550.

In the present embodiment, the case member 192 can be opened and closed with respect to the culture device sub-main body 140; however, not limited to this structure, the case member 192 may be secured to the culture device sub-main body 140. In this case, the case member 192 is required to have an opening formed on a side face and a lid for closing the opening of the side wall so as to bring in and take out the sample tray 550 and a humidifying pad 214. Moreover, the case member 192 may be designed so that one portion of the bottom has an opening with the opening being closed when it is attached to the culture device sub-main body 140.

Figure 12:
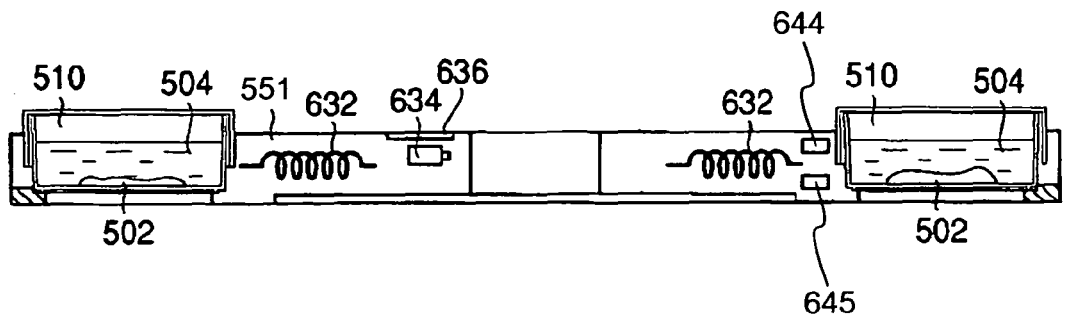
FIG. 12 is a sectional view that schematically shows an inner structure of a sample tray according to a second embodiment of the present invention.

The second embodiment is directed to another sample tray 551 that can replace the sample tray 550 shown in FIG. 7. FIG. 12 schematically shows an inner structure of the sample tray of the second embodiment of the present invention on the same sectional view of FIG. 7. In FIG. 12, those members indicated by the same reference numerals as the members shown in FIG. 7 are respectively the same members; therefore, the detailed description thereof is not repeated.

As shown in FIG. 12, in addition to the structure of the sample tray 550 of the first embodiment, the sample tray 551 of the second embodiment is provided with a temperature sensor 644 used for detecting the temperature of the sample tray 551 and a control unit 645 used for controlling the heater 632 based upon information obtained from the temperature sensor 644. Both of the temperature sensor 644 and the control unit 645 are installed inside the sample tray 550. The other structures are the same as those of the first embodiment.

The control unit 645 on/off controls the heater 632 so that, for example, when the temperature detected by the temperature sensor 644 becomes lower than 37° C., the control unit 645 starts driving the heater 632 and, when the temperature detected by the temperature sensor 644 becomes higher than 37° C., the control unit 645 stops driving the heater 632. The method of the control is not limited to the on/off control, and any other appropriate controlling method such as a Proportional-Integral-Derivative (PID) control may be used.

In the second embodiment, during a period in which the sample tray 551 has been removed from the tray attaching unit 252 of the tray holding mechanism 250 so as to exchange culture mediums, the temperature of the sample tray 551 is positively controlled to an optimal temperature (for example, 37° C.) for cultured cells 502 by the temperature sensor 644 and the control unit 645. For this reason, the cultured cells 502 within the sample 510 can be maintained at an optimal temperature, without being influenced by the environmental temperature. Consequently, it becomes possible to prevent more effectively the cultured cells 502 inside the sample 510 from being exposed to inappropriate temperatures and consequently damaged in comparison with the first embodiment. Here, in order to detect the temperature of the cultured cells 502 as accurately as possible, the temperature sensor 644 is preferably installed near the sample 510.

Figure 13:
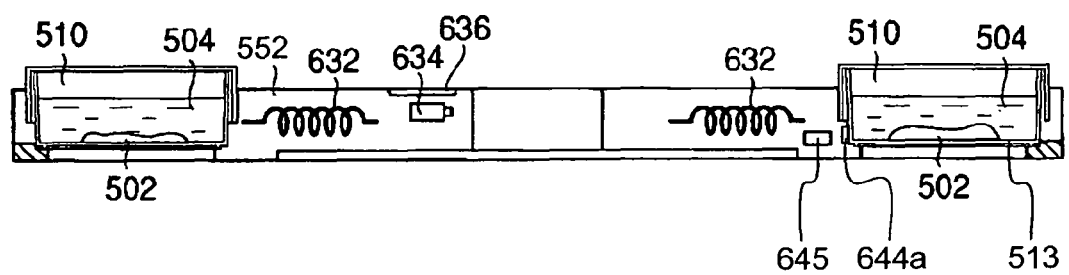
FIG. 13 is a sectional view that schematically shows an inner structure of a sample tray and a container according to a third embodiment of the present invention.

The third embodiment is directed to another sample tray 552 and another container 513 that can replace the sample tray 550 shown in FIG. 7 and the container 512 shown in FIG. 6. FIG. 13 schematically shows an inner structure of the sample tray 552 and the container 513 according to the third embodiment on the same sectional view as FIG. 7. In FIG. 13, those members indicated by the same reference numerals as the members shown in FIG. 7 are respectively the same members; therefore, the detailed description thereof is not repeated.

As shown in FIG. 13, in addition to the structure of the sample tray 550 and the container 512 of the first embodiment, the sample tray 552 and the container 513 of the third embodiment are provided with a temperature-measuring resistor 644a installed in a container main body 514 of the container 513 and a control unit 645 used for controlling the heater 632 based upon information obtained from the temperature-measuring resistor 644a. The control unit 645 is installed inside the sample tray 552. The other structures are the same as those of the first embodiment. Here, the temperature-measuring resistor 644a may be attached to the lid 518.

The control unit 645 on/off controls the heater 632 so that, for example, when the temperature detected by the temperature-measuring resistor 644a becomes lower than 37° C., the control unit 645 starts driving the heater 632 and, when the temperature detected by the temperature-measuring sensor 644a becomes higher than 37° C., the control unit 645 stops driving the heater 632. The method of the control is not limited to the on/off control, and any other appropriate controlling method such as a PID control may be used. Here, the control unit 645 determines the temperature by, for example, a resistance value of the temperature-measuring resistor 644a.

In the third embodiment, during a period in which the sample tray 552 has been removed from the tray attaching unit 252 of the tray holding mechanism 250 so as to exchange culture mediums, the temperature of the sample tray 552 is positively controlled to an optimal temperature (for example, 37° C.) for cultured cells 502 by the temperature-measuring resistor 644a attached to the container 513 and the control unit 645. For this reason, the cultured cells 502 within the sample 510 can be maintained at an optimal temperature, without being influenced by the environmental temperature. Moreover, since the temperature-measuring resistor 644a is attached to the container 513, the temperature of the cultured cells 502 can be detected more accurately, and it becomes possible to prevent more effectively the cultured cells 502 inside the sample 510 from being exposed to inappropriate temperatures and consequently damaged in comparison with the second embodiment.

Figure 14:
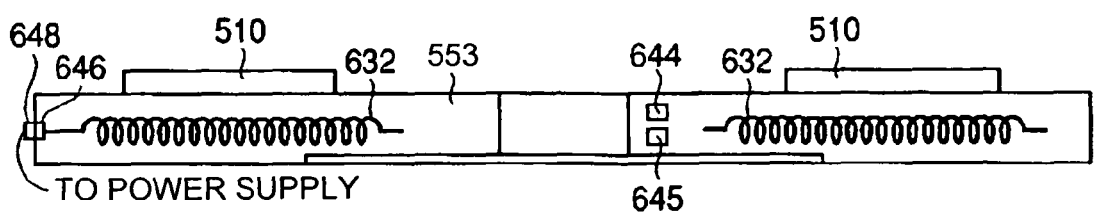
FIG. 14 is a sectional view that schematically shows an inner structure of a sample tray according to a fourth embodiment of the present invention.

The fourth embodiment is directed to still another sample tray 553 that can replace the sample tray 550 shown in FIG. 7. FIG. 14 schematically shows an inner structure of the sample tray according to the fourth embodiment.

As shown in FIG. 14, the sample tray 553 of the fourth embodiment is provided with a heater 632 that heats the sample tray 553 and a connector 646 that is electrically connected to the heater 632. The heater 632 may be prepared as, for example, a resistor that generates heat in response to a power supply in the same manner as the first embodiment; however, not limited to this, any desired electric element that is temperature-adjustable, such as a Peltier element, may be used. The connector 646, which is connected to an energy supplying unit 648 connected to a power supply, not shown, in the clean bench, sends energy supplied from the energy supplying unit 648 to the heater 632.

The sample tray 553 is further provided with a temperature sensor 644 used for detecting the temperature of the sample tray 553 and a control unit 645 that controls the heater 632 based upon information obtained by the temperature sensor 644. The control unit 645 controls the heater 632 by using an appropriate control method such as an on/off control and a PID control, in the same manner as the second embodiment.

In the fourth embodiment, the heater 632, which receives an energy supply from the energy supplying unit 648 inside the clean bench that is connected to the connector 646, generates heat so that the temperature of the sample tray 553 is positively controlled to an optimal temperature (for example, 37° C.) for cultured cells 502 by the temperature sensor 644 and the control unit 645. For this reason, the cultured cells 502 within the sample 510 can be maintained at an optimal temperature, without being influenced by the environmental temperature.

During the shift between the culture observation apparatus 100 and the clean bench, the sample tray 553 is not heated; however, in general, the culture observation apparatus 100 and the clean bench are placed close to each other in most cases, and in such a state, the sample tray 553 of the fourth embodiment is allowed to sufficiently function effectively.

Figure 15:
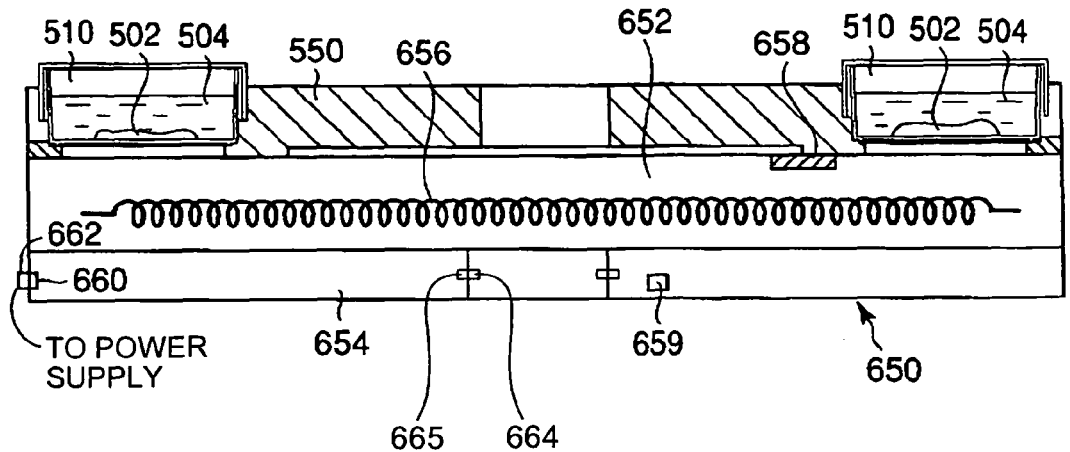
FIG. 15 is a drawing that schematically shows a sample tray heat-insulating device according to a fifth embodiment of the present invention.

The fifth embodiment is directed to a sample tray heat-insulating device used for heat-insulating the sample tray 550 shown in FIG. 1 in the clean bench. FIG. 15 schematically shows a sample tray heat-insulating device according to the fifth embodiment of the present invention.

As shown in FIG. 15, the sample tray heat-insulating device 650 of the fifth embodiment is provided with a sample tray mounting base 652 on which the sample tray 550 is mounted and a base 654 that rotatably supports the sample tray mounting base 652. The sample tray mounting base 652 is provided with a heater 656 used for heating the sample tray mounting base 652 and a slip ring 664, and the base 654 is provided with a connector 660 that is electrically connected to the heater 656 and a slip ring 665 that is made in contact with the slip ring 664 of the sample tray mounting base 652.

The heater 656 may be prepared as, for example, a resistor that generates heat in response to a power supply in the same manner as the first embodiment; however, not limited to this, any desired electric element that is temperature-adjustable, such as a Peltier element, may be used. The connector 660, which is connected to an energy supplying unit 662 connected to a power supply, not shown, in the clean bench, sends energy supplied from the energy supplying unit 662 to the heater 656 through the slip ring 665 of the base 654 and the slip ring 664 of the sample tray mounting base 652. Here, the slip ring 665 of the base 654 and the slip ring 664 of the sample tray mounting base 652 can be maintained in an electrically connected state even when the sample tray mounting base 652 is rotated on the base 654.

The sample tray heat-insulating device 650 is further provided with a temperature sensor 658 used for detecting the temperature of the sample tray 550 mounted on the sample tray mounting base 652 and a control unit 659 that controls the heater 656 based upon information obtained by the temperature sensor 658. The control unit 659 controls the heater 656 by using an appropriate control method such as an on/off control and a PID control, in the same manner as the second embodiment.

In the sample tray heat-insulating device 650 of the fifth embodiment, the heater 656, which receives an energy supply from the energy supplying unit 662 inside the clean bench that is connected to the connector 660, through the slip ring 664 and the slip ring 665, generates heat so that the temperature of the sample tray 550 is positively controlled to an optimal temperature (for example, 37° C.) for cultured cells 502 by the temperature sensor 658 and the control unit 659. For this reason, the cultured cells 502 within the sample 510 can be maintained at an optimal temperature, without being influenced by the temperature inside the clean bench. Moreover, by using the slip ring 664 and the slip ring 665, it becomes possible to eliminate the necessity of wiring used for connecting the sample tray mounting base 652 to the base 654, and consequently to prevent problems such as entangled wiring.

Preferably, the sample tray heat-insulating device 650 is connected to a control unit 420 such as a personal computer that controls the entire apparatus of the culture observation apparatus 100 so that based upon information of culture-medium exchanging time stored in the control unit 420, the heater 656 is preferably driven a predetermined time before the start of the culture medium exchanging operation. Moreover, the sample tray mounting base 652 is preferably made in contact with the side face and the concave plane 556 or the like of the opening 554 of the sample tray 550, in order to increase the contact area to the sample tray 550.

During the shift between the culture observation apparatus 100 and the clean bench, the sample tray 550 is not heated; however, in general, the culture observation apparatus 100 and the clean bench are placed close to each other in most cases, and in such a state, the sample tray 550 of the fifth embodiment is allowed to sufficiently function effectively.

The sample tray mounting base 652 is rotatable with respect to the base 654 so that the operator can easily place a desired sample 510 in front of him or her and the culture-medium exchanging operation is consequently carried out comparatively easily.

In the culture observation-apparatus 100 shown in FIG. 1, since the inside of the sample 510 is controlled to about 95% in humidity in the culture space 202, condensation of dew easily occurs even with a temperature drop of 1° C. of the lid 518 with respect to the sample tray 550. For this reason, during the culture-medium exchanging operation, the temperature of the lid 518 sometimes drops to cause dew condensation inside thereof, with the result that immediately after the culture-medium exchanging operation, the cultured cells inside the sample 510 becomes invisible temporarily.

Moreover, the temperature drop of the lid 518 tends to cause a temperature drop of air enclosed by the container 512 and the lid 518 and the subsequent temperature drop of the sample 510, resulting in a serious problem of damages to the sample.

Figure 16:
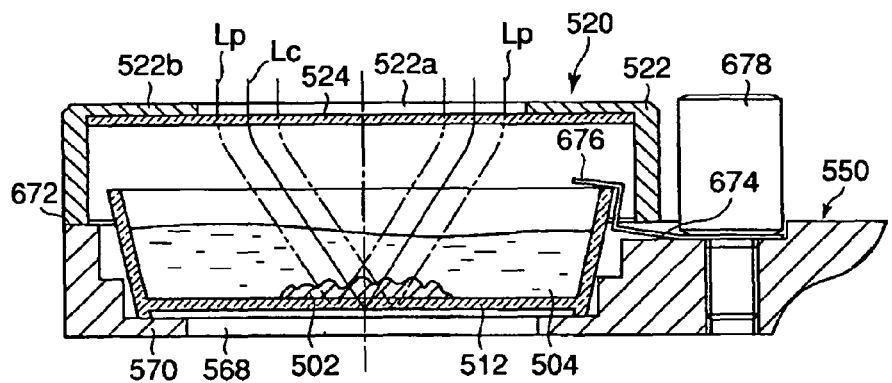
FIG. 16 is a drawing that shows a sectional structure of a sample tray, a container, and a lid according to a sixth embodiment of the present invention.
Figure 17:
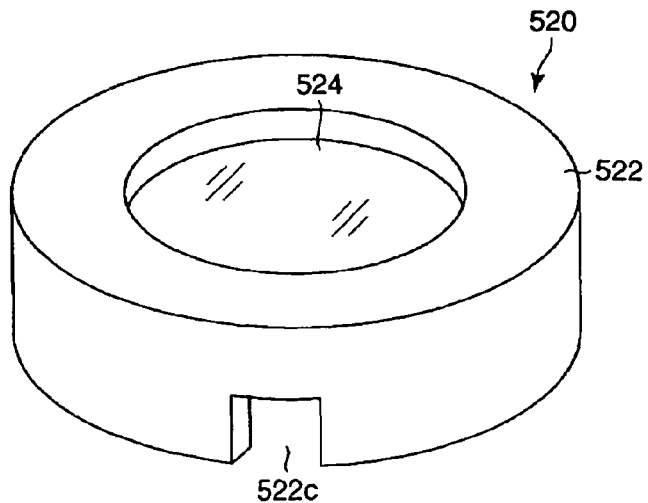
FIG. 17 is a perspective view of the lid shown in FIG. 16.

In order to solve the above-mentioned problems, the sixth embodiment is directed to a lid which is hardly subjected to dew condensation, and used for covering the container 512 held on the sample tray 550. FIG. 16 shows a sectional structure of a sample tray and a container according to a sixth embodiment of the present invention. FIG. 17 is a perspective view of the lid shown in FIG. 16.

As shown in FIGS. 16 and 17, the lid 520 of the sixth embodiment is provided with a lid main body 522 having an opening 522a with a round shape and a transparent plate 524 that covers the opening 522a of the lid main body 522. The lid main body 522 has a high thermal conductivity, and is made of metal such as aluminum, although not limited to this. The transparent plate 524 is made of, for example, a glass plate, although not limited to this.

As shown in FIG. 16, in order to make the contact area between the lid main body 522 and the transparent plate 524 as large as possible, the opening 522a of the lid main body 522 is designed so as not to be unnecessarily large by taking an observation range determined by the locus of illuminating light rays and the shifting range of the sample tray 550 into consideration. In FIG. 16, each solid line Lc indicates a locus of the illuminating light ray when the center of the observation range is located on the light axis of the objective lens 312, and each virtual line Lp indicates a locus of the illuminating light ray when the end of the observation range is located on the light axis of the objective lens 312. In other words, the upper face of the transparent plate 524 is covered with the opening circumferential portion 522b of the lid main body 522 except for the range that allows illuminating light rays to pass and the peripheral portion thereof.

Moreover, as shown in FIG. 17, the lid main body 522 has cut-out portions 522c at some portions on the side wall having a cylinder shape so as to deliver a sufficient amount of carbon dioxide to the cultured cells 502.

As shown in FIG. 16, the sample tray 550 has a lid mounting face 672 on which the lid 520 is mounted, on the periphery of each of concave sections 570 that support the container 512. The sample tray 550 is provided with a container supporting mechanism used for holding the container 512 for each of the concave sections 570. The container holding mechanism is constituted by a plate spring 676 used for pressing the container 512 and a securing screw 678 used for securing the plate spring 676 onto the spring mount face 674 of the sample tray 550. The spring mount face 674 is located at a position lower than the lid mounting face 672. The plate spring 676 is bent into a crank shape, and extends between the container 512 and the lid 520 so that the resulting pressing force is applied onto the upper face of the container 512. Thus, the container 512 is secured onto the sample tray 550. The lid 520 can be opened and closed without the necessity of applying any force to the plate spring 676. Therefore, upon exchanging culture mediums, there is no possibility of positional deviations of the container 512 with respect to the sample tray 550.

In the sixth embodiment, upon mounting the lid 520 on the sample tray 550 to cover the container 512, the lid main body 522 is directly made in face-contact with the lid mounting face 672 of the sample tray 550. For this reason, the heat of the sample tray 550 is effectively transmitted to the lid main body 522. Moreover, the transparent plate 524 is made in contact with the lid main body 522 with a comparatively large area on the peripheral portion 522b of the opening. For this reason, the heat of the lid main body 522 is also effectively transmitted to the transparent plate 524. With this arrangement, the temperature drop of the transparent plate 524 of the lid 520 with respect to the sample tray 550 is reduced so that the occurrence of dew condensation onto the transparent plate 524 is desirably suppressed. Therefore, when the sample tray 550 is returned to the culture observation apparatus 100, the observation can be started immediately without the necessity of waiting for disappearance of dew condensation.

Moreover, it becomes possible to prevent cells from being damaged.

Figure 18:
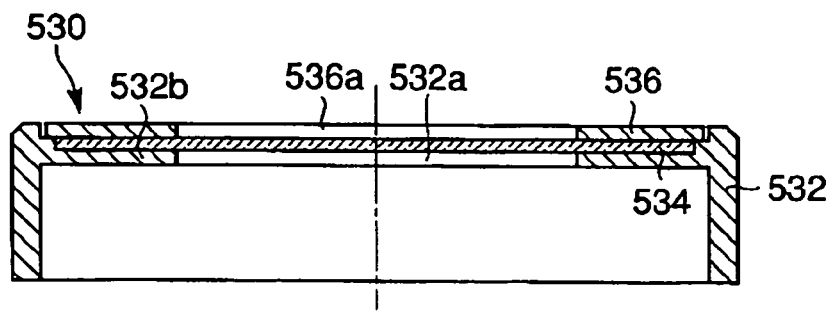
FIG. 18 is a drawing that shows a sectional structure of a lid according to a seventh embodiment of the present invention.

The seventh embodiment is directed to another lid that can replace the lid as shown in FIG. 16. FIG. 18 shows a sectional structure of a lid according to the seventh embodiment.

As shown in FIG. 18, the lid 530 of the seventh embodiment is provided with a lid main body 532 that has an opening 532a with a round shape, a transparent plate 534 that covers the opening 532a of the lid main body 532 and a pressing plate 536 that has an opening 536a with a round shape. Both of the lid main body 532 and the pressing plate 536 have a high thermal conductivity, and are made of, for example, metal such as aluminum, although not particularly limited thereto. The transparent plate 534 is made of, for example, a glass plate, although not particularly limited thereto.

In the same manner as the sixth embodiment, the opening 532a of the lid main body 532 and the opening 536a of the pressing plate 536 are designed so as not to become unnecessarily large by taking the observation range determined by the locus of illuminating light rays and the shifting range of the sample tray 550 into consideration.

The transparent plate 534 is supported by the peripheral portion 532b of the opening of the lid main body 532, and pressing plate 536 is mounted on the transparent plate 534. For this reason, the transparent plate 534 is made in contact with the lid main body 532 with a comparatively large area on the peripheral portion 532b of the opening of the lid main body 532, and also made in contact with the pressing plate 536 with a comparatively large area.

In the same manner as the sixth embodiment, the lid 530 is designed so that when mounted on the sample tray 550 to cover the container 512, the lid main body 532 is directly made in face-contact with the lid mounting face 672 of the sample tray 550.

In the lid 530 of the seventh embodiment, both of the upper face and the lower face of the transparent plate 534 are partially made in face-contact with the lid main body 532 and the pressing plate 536. Therefore, the heat of the sample tray 550 is transmitted to the transparent plate 534 more effectively than that of the sixth embodiment. With this arrangement, the temperature drop of the transparent plate 534 of the lid 530 with respect to the sample tray 550 is more effectively reduced, and the occurrence of dew condensation onto the transparent plate 534 is consequently reduced more effectively. Therefore, when the sample tray 550 is returned to the culture observation apparatus 100, the observation can be started immediately without the necessity of waiting for disappearance of dew condensation.

Moreover, it becomes possible to prevent cells from being damaged.

Figure 19:
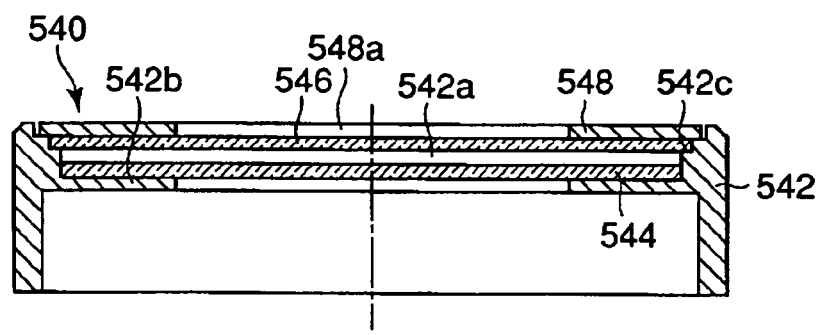
FIG. 19 is a drawing that shows a sectional structure of a lid according to an eighth embodiment of the present invention.

The eighth embodiment is directed to still another lid that can replace the lid as shown in FIG. 16. FIG. 19 shows a sectional structure of a lid according to the eighth embodiment.

As shown in FIG. 19, the lid 540 of the eighth embodiment is provided with a lid main body 542 that has an opening 542a with a round shape, a transparent plate 544 and a transparent plate 546 that seal the opening 542a of the lid main body 542 and a pressing plate 548 that has an opening 548a with a round shape. Both of the lid main body 542 and the pressing plate 548 have a high thermal conductivity, and are made of, for example, metal such as aluminum, although not particularly limited thereto. The transparent plates 544 and 546 are made of, for example, glass plates, although not particularly limited thereto.

In the same manner as the sixth embodiment, the opening 542a of the lid main body 542 and the opening 548a of the pressing plate 548 are designed so as not to become unnecessarily large by taking the observation range determined by the locus of illuminating light rays and the shifting range of the sample tray 550 into consideration.

The transparent plate 544 is supported by the peripheral portion 542b of the opening of the lid main body 542.

The transparent plate 546, which has a size larger than that of the transparent plate 544, is supported with a gap from the transparent plate 544 by a step difference 542c placed on the periphery of the opening peripheral portion 542b. The pressing plate 548 is mounted on the transparent plate 546. The transparent plate 544 is made in contact with the lid main body 542 with a comparatively large area along the opening peripheral portion 542b of the lid main body 542. The pressing plate 548 is also made in contact with the pressing plate 548 with a comparatively large area.

In the same manner as the sixth embodiment, the lid 540 is designed so that when mounted on the sample tray 550 to cover the container 512, the lid main body 542 is directly made in face-contact with the lid mounting face 672 of the sample tray 550.

In the lid 540 of the eighth embodiment, since the transparent plate 544 and the pressing plate 548 are respectively made in contact with the lid main body 542 and the pressing member 548 with comparatively large areas, the heat of the sample tray 550 is transmitted to the transparent plate 544 and the pressing plate 548 effectively. Moreover, by a heat-insulating effect of an air layer between the transparent plate 544 and the pressing plate 548, the temperature of the outside air is hardly transmitted to the inside transparent plate 544. With this arrangement, the temperature drop of the transparent plate 544 of the lid 540 with respect to the sample tray 550 is effectively reduced, and the occurrence of dew condensation onto the transparent plate 544 is consequently reduced more effectively. Therefore, when the sample tray 550 is returned to the culture observation apparatus 100, the observation can be started immediately without the necessity of waiting for disappearance of dew condensation. Moreover, by forming the gap between the transparent plate 544 and the pressing plate 548 into a vacuum state, the heat-insulating effect can be further improved.

Moreover, it becomes possible to prevent cells from being damaged.

Figure 20:
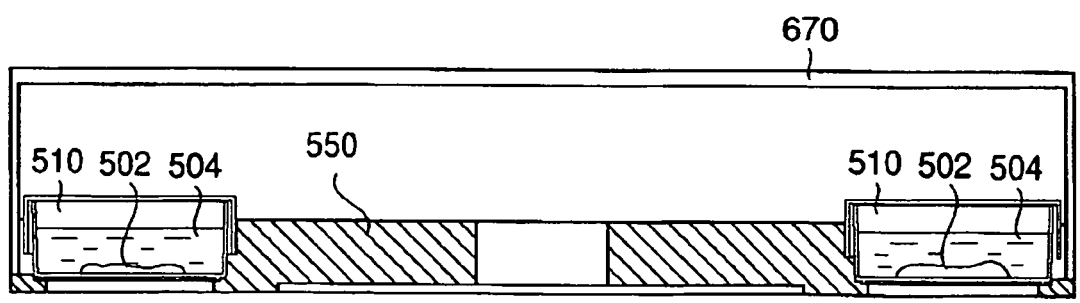
FIG. 20 is a drawing that shows a sectional structure of a lid according to a ninth embodiment of the present invention.

The ninth embodiment is directed to a lid used for covering a sample tray that holds a container in which cultured cells and a culture medium are held. FIG. 20 shows a sectional structure of the lid according to the ninth embodiment.

As shown in FIG. 20, the lid 670 of the ninth embodiment is made from a material that is superior in heat insulating property, and covers the entire upper space of a sample tray 550 when mounted on the sample tray 550. Thus, it covers the sample tray 550 that holds a container 512 housing cultured cells 502 and a culture medium 504.

The lid 670 is mounted on the sample tray 550 while the sample tray 550 is shifted between the culture observation apparatus 100 and the clean bench. With this arrangement, the temperature drop of the sample 510 (that is, the container 512 housing the cultured cells 502 and the culture medium 504, as well as the lid 518 covering these) held in the sample tray 550 is effectively suppressed. Thus, the temperature drop of the lid 518 with respect to the sample tray 550 is suppressed, and the occurrence of dew condensation onto the lid 518 is effectively prevented. Therefore, when the sample tray 550 is returned to the culture observation apparatus 100, the observation can be started immediately without the necessity of waiting for disappearance of dew condensation.

While the invention has been described in detail and with reference to specific examples thereof, it will be apparent to one skilled in the art that various changes and modifications can be made therein without departing from the spirit and scope thereof.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A culture observation apparatus, which is used for observing a cultured cell while culturing the cell, comprising:
    a culture device that forms a culture space which is controlled to be an environment suitable for culturing the cultured cell;
    a sample tray that holds a container for housing the cultured cell and a culture medium, the sample tray being removable from the culture space together with the container housing the cultured cell for exchanging the culture medium;
    a microscope for observing the cultured cell;
    a tray holding mechanism that holds the sample tray in the culture space in a detachable manner with good reproducibility;
    and
    a shifting mechanism that relatively shifts the sample tray held by the tray holding mechanism and a light axis of the microscope along a plane that is orthogonal to the light axis,
    wherein the sample tray comprises a heater used for heating the sample tray at least when the sample tray is removed from the culture space together with the container housing the cultured cell for exchanging the culture medium, and wherein the sample tray is electrically connectable to an energy supplying unit that supplies energy to the sample tray.

2. The culture observation apparatus according to claim 1, wherein:
    the sample tray includes an energy storing unit used for driving the heater, and
    the energy supplying unit is installed in the tray holding mechanism, and supplies energy stored in the energy storing unit, when the sample tray is held in the tray holding mechanism.

3. The culture observation apparatus according to claim 2, wherein:
   the sample tray further includes a switch that controls the supply of energy from the energy storing unit to the heater, and
   the switch allows the energy storing unit to start supplying energy to the heater, when the sample tray is separated from the tray holding mechanism.

4. The culture observation apparatus according to claim 1, wherein the sample tray includes a connector that is electrically connectable to the energy supplying unit.

5. The culture observation apparatus according to claim 1, wherein the sample tray further includes:
   a temperature sensor that detects a temperature of the sample tray, and
   a control unit that controls the heater based upon information obtained by the temperature sensor.

6. The culture observation apparatus according to claim 1, wherein:
   the container for housing the cultured cell and the culture medium includes a temperature-measuring resistor, and
   the sample tray includes a control unit that controls the heater based upon a resistance value or a temperature detected by the temperature-measuring resistor.

7. A sample tray heat-insulating device that heat-insulates a sample tray which holds, at least when the sample tray is in a culture space, a container for housing a cultured cell and a culture medium, the sample tray heat-insulating device comprising:
   a sample tray mounting base on which the sample tray, that is removed from the culture space together with the container housing the cultured cell for exchanging the culture medium, is mountable to support the sample tray from below;
   a heater that heats the sample tray mounting base; and
   a base that rotatably supports the sample tray mounting base.

8. The sample tray heat-insulating device according to claim 7, wherein:
   the sample tray mounting base is electrically connected to the base through a slip ring, and
   the heater receives energy through the slip ring.

9. The sample tray heat-insulating device according to claim 7, further comprising:
   a temperature sensor that detects a temperature of the sample tray mounted on the sample tray mounting base; and
   a control unit that controls the heater based on information obtained by the temperature sensor.

10. A culture observation apparatus, which is used for observing a cultured cell while culturing the cell, comprising:
   a culture device that forms a culture space which is controlled to be an environment suitable for culturing the cultured cell;
   a container for housing the cultured cell and a culture medium;
   a sample tray that holds the container;
   a microscope for observing the cultured cell;
   a tray holding mechanism that holds the sample tray in the culture space in a detachable manner with good reproducibility;
   a shifting mechanism that relatively shifts the sample tray held by the tray holding mechanism and a light axis of the microscope along a plane that is orthogonal to the light axis;
   a heater used for heating the sample tray;
   an energy supplying unit that supplies energy to the sample tray; and
   a lid which covers the container that is held on the sample tray and that houses the cultured cell and the culture medium, wherein the lid comprises:
   a lid main body having an opening and having a high thermal conductivity; and
   a transparent plate that seals the opening of the lid main body,
   wherein when the sample tray is removed from the culture space together with the lid and the container housing the cultured cell for exchanging the culture medium, the lid main body is in contact with the sample tray, the heater heats the sample tray and the lid main body, and the sample tray heat-insulates the cultured cell and the culture medium.

11. The culture observation apparatus according to claim 1, wherein:
   the culture device comprises a culture device main-body and a culture device sub-main body, and
   the culture observation apparatus further comprises a main-body supporting base.

12. The culture observation apparatus according to claim 11, wherein the main-body supporting base supports the culture device main-body and the culture device sub-main body.

13. The culture observation apparatus according to claim 11, wherein the culture device sub-main body comprises:
   a lower base portion that is supported by the main-body supporting base;
   a side wall surrounding an upper periphery of the lower base portion; and
   an upper base portion that covers an opening on an upper side of the side wall.

14. The culture observation apparatus according to claim 13, wherein:
   the culture device main body comprises a box-shaped case member with an opening on a bottom face thereof, and
   the case member is attached to the side wall of the culture device sub-main body so as to be opened and closed with respect to the culture device sub-main body.

15. The culture observation apparatus according to claim 14, wherein when the case member is closed, the case member and the culture device sub-main body define the culture space for culturing the cell.

16. The culture observation apparatus according to claim 13, wherein the microscope and the shifting mechanism are provided substantially below the upper base portion of the culture device sub-main body.

17. The culture observation apparatus according to claim 1, wherein the sample tray is adapted to hold a plurality of containers, and each container is adapted to house a given cultured cell and a given culture medium.

18. The culture observation apparatus according to claim 1, further comprising a lid that covers the container, and wherein the lid and the container are both optically transparent.

19. The sample tray heat-insulating device according to claim 9, wherein the control unit controls the heater based on a predetermined culture medium exchanging time so that the heater is driven a predetermined time before start of a culture medium exchanging operation.

20. The culture observation apparatus according to claim 10, wherein the lid further comprises a pressing plate having an opening, and wherein:
   the opening of the pressing plate substantially coincides with and is directly above the opening of the lid main body, and the transparent plate or the transparent plate and a second transparent plate are provided between the opening of the pressing plate and the opening of the lid main body, thereby sealing the opening of the pressing plate and the opening of the lid main body.

21. The culture observation apparatus according to claim 10, wherein:

the culture device comprises a culture device main-body and a culture device sub-main body, the culture observation apparatus further comprises a main-body supporting base that supports the culture device main-body and the culture device sub-main body, the culture device main body comprises a box-shaped case member with an opening on a bottom face thereof, the case member is attached to a side wall of the culture device sub-main body so as to be opened and closed with respect to the culture device sub-main body, when the case member is closed, the case member and the culture device sub-main body define the culture space for culturing the cell, and the sample tray is adapted to hold a plurality of containers, and each container is adapted to house a given cultured cell and a given culture medium.

22. The culture observation apparatus according to claim 21, wherein:

the culture device sub-main body comprises:

a lower base portion that is supported by the main-body supporting base;

the side wall surrounding an upper periphery of the lower base portion; and an upper base portion that covers an opening on an upper side of the side wall, and the microscope and the shifting mechanism are provided substantially below the upper base portion of the culture device sub-main body.

* * * * *